United States Patent [19]

Campbell

[11] 4,031,072
[45] June 21, 1977

[54] TETRAPEPTIDES

[75] Inventor: Alfred Campbell, Ann Arbor, Mich.

[73] Assignee: Parke, Davis & Company, Detroit, Mich.

[22] Filed: Mar. 1, 1976

[21] Appl. No.: 662,407

[52] U.S. Cl. .............. 260/112.5 LH; 260/112.5 R; 424/177

[51] Int. Cl.² ..................................... C07C 103/52

[58] Field of Search .......... 260/112.5 R, 112.5 LH

[56] References Cited

UNITED STATES PATENTS 3,725,380  4/1973  Konig et al. ................. 260/112.5 R

OTHER PUBLICATIONS

J. M. Stewart and J. D. Young, "Solid Phase Peptide Synthesis", Freeman and Co., San Francisco, 1969, pp. 9–13.

J. D. Roberts and M. C. Caserio, "Basic Principles of Organic Chemistry", Benjamin, Inc., N.Y., 1965, pp. 531, 563–564.

E. Schroder and K. Lubke, "The Peptides", vol. 1, Academic Press, N.Y., 1965, pp. 79–80.

*Primary Examiner*—Delbert R. Phillips
*Attorney, Agent, or Firm*—Stephen Raines; David B. Ehrlinger; George M. Richards

[57] ABSTRACT

New tetrapeptides having the formula A-Pro-Pro-Tyr(benzyl)-Ser(benzyl)-$R_1$ wherein A is t-butoxycarbonyl, cyclohexylcarbonyl, benzyloxycarbonyl and p-nitrobenzyloxycarbonyl; Pro is D-Pro or L-Pro; Tyr(benzyl) is D-Tyr(benzyl) or L-Tyr(benzyl); Ser(benzyl) is D-Ser(benzyl) or L-Ser(benzyl) and $R_1$ is lower alkoxy, hydrazino, amino, lower alkylamino or di(lower alkyl)amino.

8 Claims, No Drawings

TETRAPEPTIDES

The present invention relates to new peptide compounds that are useful as luteinizing hormone releasing factor antagonists and to methods for their production. More particularly, the invention relates to new N-protected tetrapeptides that are represented by the formula A-Pro-Pro-Tyr(benzyl)-Ser(benzyl)-R₁    I wherein A is t-butoxycarbonyl, cyclohexylcarbonyl, benzyloxycarbonyl or p-nitrobenzyloxycarbonyl; Pro is L-Pro or D-Pro; Tyr(benzyl) is L-Tyr(benzyl) or D-Tyr(benzyl); Ser(benzyl) is L-Ser(benzyl) or D-Ser(benzyl) and R₁ is lower alkoxy, hydrazino, amino, lower alkylamino or di(lower alkyl)amino.

In formula I, the conventional symbols for amino acid residues of peptide compounds linked thereto are used and each is intended to have the following meaning: L-Pro, L-prolyl; D-Pro, D-prolyl; L-Tyr(benzyl), L-tyrosyl(benzyl); D-Tyr(benzyl), D-tyrosyl(benzyl); L-Ser(benzyl), L-seryl(benzyl) and D-Ser(benzyl), D-seryl(benzyl). In addition, the term "lower alkyl" is intended to mean a straight, branched or cyclic hydrocarbon moiety of up to six carbon atoms, such as methyl, ethyl, isopropyl and cyclopropyl and "lower alkoxy" is intended to mean an alkoxy group having a straight, branched or cyclic hydrocarbon moiety of up to 6 carbon atoms, such as methoxy, ethoxy and isopropoxy. These symbols and terms will also be used in the formulae that follow for other compounds and each such symbol or term should be understood to have the meaning given above.

In accordance with this invention, compounds of the formula I, wherein A is as previously defined and R₁ is lower alkoxy, are produced by removing a protected tetrapeptide from a resin complex of the following structure A-Pro-Pro-Tyr(benzyl)-Ser(benzyl)-resin    II wherein said resin is a resin employed in solid phase peptide syntheses, such as those disclosed in a text by Stewart and Young, "Solid Phase Peptide Synthesis", W. H. Freeman & Company, San Francisco, 1969, which is incorporated by reference, preferably the resin is a crosslinked copolymer comprising 98 to 99 percent polystyrene crosslinked with 1 to 2 percent divinylbenzene, which is attached to the protected tetrapeptide through a methyleneoxy bridge wherein the methylene group is attached to the polymeric portion of the resin and the oxygen atom is attached to the protected tetrapeptide and A and R₁ are as previously defined; by treating said resin of the formula II with a lower alkyl alcohol in the presence of tertiary amine, such as triethylamine or tripropylamine.

The resin complex is suspended in an excess of the lower alkyl alcohol, preferably methanol for periods of from about 10 hours to 4 days, preferably 16 to 24 hours, at about 15° to about 35° C.

While a large excess of the lower alkyl alcohol is preferred, only a catalytic amount of tertiary amine is required; however, larger amounts of amine are preferred, such as about 10 percent volume/volume based on the amount of lower alkyl alcohol employed.

While it is not a preferred procedure, compounds of the formula I wherein R₁ is hydrazino, amino, lower alkylamino or di(lower alkyl)amino may be prepared by reacting compounds of the formula II wherein A is as previously defined with hydrazine, ammonia, lower alkylamine or di(lower alkyl)amine.

The resin complex is suspended in a solvent, such as methanol, ethanol, dimethylformamide, etc., at a temperature of from about 0° to 50° C. for periods of from 12 hours to 10 days. When employing less reactive amines the preferred solvent is dimethylformamide.

The complex resins of the formula II are prepared by coupling a protected amino acid of the formula A-Pro-OH    III wherein A is as previously defined, with complex resins of the formula Pro-Tyr(benzyl)-Ser(benzyl)-resin    IV in an organic solvent, such as dichloromethane with the aid of dicyclohexylcarbodiimide. The three reactants may be used in about equimolar quantitites, but excess amounts of the protected amino acid and dicyclohexylcarbodiimide are sometimes advantageous. The reaction is generally conducted at about room temperature for a period of from about fifteen minutes to about 16 hours.

The complex resins of the formula IV are prepared by treating complex resins of the formula t-butoxycarbonyl-Pro-Tyr(benzyl)-Ser(benzyl)-resin    V with a large excess of trifluoroacetic acid utilizing dichloromethane as the solvent at temperatures of from 20° C. to 30° C. for about 10 minutes, followed by neutralization of the trifluoroacetic acid salt with a base such as triethylamine.

The complex resins of formula V are prepared by coupling t-butoxycarbonyl-Pro-OH to complex resins of the formula Tyr(benzyl)-Ser(benzyl)-resin    VI using the reaction procedure described for the preparation of compounds of the formula II.

The complex resins of the formula VI are prepared by treating the complex resins of the formula t-butoxycarbonyl-Tyr(benzyl)-Ser(benzyl)-resin    VII with trifluoroacetic acid using the reaction procedure for the preparation of compounds of the formula IV.

The complex resins of the formula VII are prepared by coupling t-butoxycarbonyl-Try(benyl)-OH to complex resins of the formula Ser(benzyl)-resin    VIII according to the procedure used for the preparation of compounds of the formula II.

The complex resins of the formula VIII are prepared by treating the complex resins of the formula t-butoxycarbonyl-Ser-resin with trifluoroacetic acid using the reaction procedure for the preparation of compounds of the formula IV.

In accordance with this invention, compounds of the formula I, wherein A is as previously described and $R_1$ is hydrazino, amino, lower alkylamino or di(lower alkyl)amino are prepared by reacting a compound of the formula I wherein $R_1$ is alkoxy, preferably methoxy, with hydrazine, ammonia, lower alkylamine or di(lower alkylamine).

The reactions are conducted at temperatures of from about 5° to 100° C. for from 3 hours to 4 days, preferably about room temperature. Generally, a large excess of hydrazine, preferably used in the form of its hydrate, or amine is used (over five fold). The reaction is usually carried out in a non-reactive solvent, such as a lower alkyl alcohol, preferably methanol or ethanol, an ether such as tetrahydrofuran or dioxane, dimethylformamide or mixtures thereof.

In addition, in accordance with this invention, compounds of the formula I, wherein A is as previously defined and $R_1$ is amino, lower alkylamino or di(lower alkyl)amino are prepared by reacting a compound of the formula A-Pro-Pro-Tyr(benzyl)-Ser(benzyl)-N$_3$   IX with ammonia, lower alkylamine or di(lower alkyl)amine in a non-reactive solvent such as dimethylformamide dioxane, tetrahydrofuran or mixtures thereof. The reaction is carried out at about −30° C. to about 0° C. for about 12 to 24 hours, preferably −20° C. to 0° C. for from 16 to 19 hours. The two reactants are used in approximately equimolar amounts although a slight excess, about 10 percent is preferred. When A is t-butoxycarbonyl, care should be taken to avoid the presence of a large excess of acid.

The azide compounds of the formula IX are normally prepared in situ by reacting a peptide hydrazide compound of the formula I wherein A is as previously defined and $R_1$ is hydrazino, with a lower alkyl nitrite, preferably isoamyl nitrite in the presence of an acid, preferably hydrochloric acid, in an inert solvent medium such as dimethylformamide, and the resultant azide is reacted further as described above without isolation. The preferred acid for use in the azide preparation is a solution of hydrogen chloride in dimethylformamide or tetrahydrofuran; between 3 and 6 equivalents of acid are used for each equivalent of the hydrazide of formula I. The preparation of the azide is carried out at a temperature between −30° C. and 0° C. Following the in situ formation of the azide of formula IX and prior to the further reaction of the peptide azide with the appropriate amine to form certain tetrapeptides of formula I, a tertiary amine such as triethylamine is added to the reaction mixture to neutralize the acid used.

Compounds of the formula I wherein A is as previously described and $R_1$ is hydrazino, amino, lower alkylamino or di(lower alkyl(amino are prepared by coupling a compound of the formula A-Pro-Pro-Tyr(benzyl)-Ser(benzyl)-OH   X with hydrazine, ammonia, lower alkylamine or di(lower alkyl)amine in an inert solvent in the presence of dicyclohexylcarbodiimide.

The above reaction is carried out using approximately equivalent amounts of reactants in a solvent such as dichloromethane, chloroform, tetrahydrofuran, dioxane or dimethylformamide, or mixtures thereof. The preferred solvent is tetrahydrofuran.

The temperature range for carrying out the reaction may be from 5° to 50° C., preferably room temperature for periods of from 10 hours to 5 days.

1-Hydroxybenzotriazole may also be used in the above reaction in addition to the dicyclohexylcarbodiimide. The 1-hydroxybenzotriazole is added in a ratio of one to two equivalents when compared to the reactants.

The compounds of the formula X are prepared by the hydrolysis of a compound of formula I wherein A is as previously defined and $R_1$ is lower alkoxy. The reaction is conducted at temperatures of from 20° to 30° C. using about 0.5 ml. of the two normal aqueous sodium hydroxide solution and 10 ml. of solvent, usually water or an alcohol such as methanol, for each millimole of ester. The compound of formula X is isolated after acidification with an aqueous solution of citric acid.

The compounds of this invention can exist in anhydrous forms as well as in solvated, including hydrated, forms. In general, the hydrated forms and the solvated forms with pharmaceutically-acceptable solvents are equivalent to the anhydrous or unsolvated form for the purposes of the invention.

Tetrapeptides of this invention were screened for LRF antagonist activity in vitro using rat anterior pituitary cell cultures as described by Vale et al. [Endocrinology, 91, 562 (1972)]. The inhibition of LRF (luteinizng hormone release factor) induced luteinizing hormone (LH) release into the culture medium is the endpoint in this in vitro bioassay.

Following are the results of the above tests on certain preferred compounds.

ACTIVITY TABLE FOR IN VITRO TEST IN RAT ANTERIOR PITUITARY CELL CULTURES

| | Molar Conc. | LH Value ng/ml. | % LH Release Inhibition |
|---|---|---|---|
| $N^\alpha$-t-butoxycarbonyl-L-prolyl-L-prolyl-O-benzyl-L-tyrosyl-O-benzyl-D-serine methyl ester | $1 \times 10^{-6}$ | 23.24 | 75 |
|  | $3.5 \times 10^{-6}$ | 30.40 | 58 |
|  | $1 \times 10^{-7}$ | 44.97 | 25 |
| LRF Control | $5 \times 10^{-10}$ | 56.01 | |
| Saline Control |  | 12.17 | |
|  | $1 \times 10^{-6}$ | 9.38 | 91 |
| LRF Control | $3.5 \times 10^{-10}$ | 27.81 | |
| Saline Control |  | 7.65 | |
| $N^\alpha$-t-butoxycarbonyl-L-prolyl-D-prolyl-O-benzyl-L-tyrosyl-O-benzyl-L-serine-N-ethylamide | $1 \times 10^{-6}$ | 18.38 | 80 |
| LRF Control | $3.5 \times 10^{-10}$ | 41.70 | |
| Saline Control |  | 12.55 | |
| $N^\alpha$-t-butoxycarbonyl-D-prolyl-L-prolyl-O-benzyl-L-tyrosyl-O-benzyl-L-seryl hydrazide | $1 \times 10^{-6}$ | 17.61 | 83 |
| LRF Control | $3.5 \times 10^{-10}$ | 41.70 | |
| Saline Control |  | 12.55 | |

The luteinizing hormone releasing factor is known to be formed in the hypothalamus of mammals, from which it is released and transported by way of the hypothalamic hypophyseal portal system to the anterior pituitary, where it stimulates the secretion of luteinizing hormone. The secretion of luteinizing hormone from the anterior pituitary in turn is known to effect ovulation in experimental animals. Thus, LRF can be used to induce ovulation in animals. For a report of the structure of LRF, which has also been referred to as luteinizing hormone releasing hormone, or LH—RH, and its biological activity, see *Science*, Vol. 174, No. 4008, October 29, 1971, pages 511–512. Thus, the tetrapeptides of this invention are useful in controlling ovulation and in restrictng fertility.

The invention is illustrated by the following examples.

EXAMPLE 1

$N^\alpha$-t-Butoxycarbonyl-L-prolyl-L-prolyl-O-benzyl-L-tyrosyl-O-benzyl-D-serine methyl ester A mixture of 50 g of chloromethylated polystyrene resin having 1.16 mmole of chlorine per gram and 25.6 g. (0.087 mol) of $N^\alpha$-t-butoxycarbonyl-O-benzyl-D-serine in one-half liter of ethanol is treated wit 8.2 g. (0.058 mol) of triethylamine and refluxed for three days. The resin is separated by filtration, washed with ethanol, water, methanol, dichloromethane and ether, successively, and then dried overnight at 40° C. giving the $N^\alpha$-t-butoxycarbonyl-O-benzyl-D-serine resin (58 g.).

A tubular flask of 400 ml. capacity, having a sintered glass disc and stopcock at one end and a suitably placed opening for addition of materials at the other is clamped to a motor which imparts a rocking motion to the flask. The flask is charged with 12.5 g. (10 mmol) of $N^\alpha$-t-buxoxycarbonyl-O-benzyl-D-serine resin and 100 ml. of dichloromethane and agitated for one half hour. The liquid is then drained from the flask by connecting a suction, through a trap, to the stopcock. The resin is retained in the flask by means of the sintered glass disc. The $N^\alpha$-t-butoxycarbonyl protecting group is removed by rocking the resin with 100 ml. of trifluoroacetic acid and 100 ml. of dichloromethane for 10 minutes. The liquid is drained from the flask and the trifluoroacetate salt of O-benzyl-D-serine resin is washed three times with 150 ml. of dichloromethane each time. The trifluoroacetate salt of the O-benzyl-D-serine resin is converted to O-benzyl-D-serine resin by the addition of 30 ml. of triethylamine in 150 ml. of cold dichloromethane and rocking the reaction for 5 minutes. The flask is drained and the resin again washed three times with 150 ml. of dichloromethane each time. The O-benzyl-L-tyrosine moiety is coupled to the O-benzyl-D-serine resin by adding 4.45 g. (12 mmol) of $N^\alpha$-t-butoxycarbonyl-O-benzyl-L-tyrosine in 100 ml. of dichloromethane, shaking for thirty minutes, adding 2.5 g. (12 mmol) of dicyclohexylcarbodiimide in 50 ml. of dichloromethane and rocking the reaction flask for 4 hours. The flask is drained and the resin washed three times with 150 ml. of dichloromethane each time. Trifluoroacetic acid (100 ml.) and dichloromethane (100 ml.) are used as above to remove the t-butoxycarbonyl protecting group and the resin drained and washed as before. Triethylamine, 20 ml. in 150 ml. of cold dichloromethane, is used to liberate the O-benzyl-L-tyrosyl-O-benzyl-D-serine resin, which is treated with 2.6 g. (12 mmol) of $N^\alpha$-t-butoxycarbonyl-L-proline in 100 ml. of dichloromethane, rocked for thirty minutes and 2.5 g. (12 mmol) of dicyclohexylcarbodiimide added in 50 ml. of dichloromethane. The coupling reaction is rocked for 4 hours, the flask drained and the resin washed two times with 150 ml. of dichloromethane each time. Trifluoroacetic acid (100 ml.) and dichloromethane (150 ml.) are again used as above to remove the t-butoxycarbonyl protecting group and the resin drained and washed as before.

Triethylamine, 20 ml. in 150 ml. of dichloromethane, is used to liberate the L-propyl-O-benzyl-L-tyrosyl-O-benzyl-D-serine resin which is treated with 2.6 g. (12 mmol) of $N^\alpha$-t-butoxycarbonyl-L-proline in 100 ml. of dichloromethane and 2.5 g. (12 mmol) of dicyclohexylcarbodiimide in 50 ml. dichloromethane as described above. The resin is then washed with 150 ml. of ethanol, agitated for twenty minutes, and poured out of the flask on a filter funnel where it is washed with ethanol and then with ether and then dried at 50° C. and under reduced pressure.

The dried resin is stirred overnight with 50 ml. of triethylamine and 500 ml. of methanol, removed by filtration and the filtrate evaporated to yield crude $N^\alpha$-t-butoxycarbonyl-L-propyl-L-propyl-O-benzyl-L-tyrosyl-O-benzyl-D-serine methyl ester. The product is a brown glass which is purified by chromatography over silica gel 60 [particle size 0.063–0.200 mm., E. Merck] in ethyl acetate solution. Selection of the appropriate fractions by thin layer chromatography and evaporation gives the pure product as an amber glass $[\alpha]_D^{23}$ −78° (c 1. methanol).

The general procedure and equipment for solid phase peptide synthesis is described by Stewart and Young, "Solid Phase Peptide Synthesis", W. H. Freeman and Company, San Francisco, 1969.

EXAMPLE 2

$N^\alpha$-t-Butoxycarbonyl-L-prolyl-L-prolyl-O-benzyl-L-tyrosyl-O-benzyl-D-serinamide $N^\alpha$-t-Butoxycarbonyl-L-prolyl-L-prolyl-O-benzyl-L-tyrosyl-O-benzyl-D-serine methyl ester, 0.5 g., is dissolved in 20 ml. of methanol and the solution saturated with anhydrous ammonia gas. The mixture is allowed to stand at room temperature for 3 days. The solvent is evapoated and the resulting crude product purified by column chromatography on silica gel using ethyl acetate-methanol (85:15) to give 0.35 g. of the amide as a glass, $[\alpha]_D^{23}$ −86.2° (c 1.01, methanol).

EXAMPLE 3

$N^\alpha$-t-Butoxycarbonyl-L-propyl-L-propyl-O-benzyl-L-tyrosyl-O-benzyl-D-serine N-ethylamide $N^\alpha$-t-Butoxycarbonyl-L-prolyl-L-prolyl-O-benzyl-L-tyrosyl-O-benzyl-D-serine methyl ester, 0.5 g., is dissolved in 50 ml. of a mixture of methanol and ethylamine (50:50). The solution is let stand at room temperature for one day. After removal of the solvent, the crude product is purified by column chromatography on silica gel using ethyl acetate-methanol (85:15) to give 0.28 g. of the amide as a glass, $[\alpha]_D^{23}$ −74° (c 1.01, methanol).

EXAMPLE 4

$N^\alpha$-t-Butoxycarbonyl-D-prolyl-D-prolyl-O-benzyl-L-tyrosyl-O-benzyl-D-serine methyl ester $N^\alpha$-t-Butoxycarbonyl-D-prolyl-D-prolyl-O-benzyl-L-tyrosyl-O-benzyl-D-serine resin is obtained by the solid phase synthetic procedure described in Example 1 by successive coupling of O-benzyl-D-serine resin 10 g. (12 mmol) with (1) 4.45 g. (12 mmol) of $N^\alpha$-t-butoxycarbonyl-L-tyrosine and 2.5 g. (12 mmol) of dicyclohexylcarbodiimide, (2) 2.6 g. (12 mmol) of $N^\alpha$-t-butoxycarbonyl-D-proline and 2.5 g. of dicyclohexylcarbodiimide and (3) 2.6 g. (12 mmol) of $N^\alpha$-t-butoxycarbonyl-D-proline and 2.5 g. (12 mmol) dicyclohexylcarbodiimide. The resin is finally washed with 150 ml. of ethanol, 150 ml. of methanol and dried at 50° under reduced pressure.

The resin is reacted with 500 ml. of methanol and 50 ml. of triethylamine to yield 4.2 g. of crude product which is purified by chromatography over silica gel using ethyl acetate; $[\alpha]_D^{23} + 52°$ (c. 1.05, methanol).

EXAMPLE 5

$N^\alpha$ -t-Butoxycarbonyl-D-prolyl-D-prolyl-O-benzyl-L-tyrosyl-O-benzyl-D-serine N-ethylamide $N^\alpha$ -t-Butoxycarbonyl-D-prolyl-D-prolyl-O-benzyl-L-tyrosyl-O-benzyl-D-serine methyl ester 0.5 g., is reacted with 20 ml. of a 50% solution of ethylamine in methanol for 24 hours and the product obtained as a glass as described in Example 3; $[\alpha]_D^{23} + 58.5°$ (c. 1, methanol).

EXAMPLE 6

$N^\alpha$ -t-Butoxycarbonyl-L-prolyl-D-prolyl-O-benzyl-L-tyrosyl-O-benzyl-L-serine methyl ester The ester is obtained by reacting 10 g., 12 mmol of $N^\alpha$ -t-butoxycarbonyl-O-benzyl-L-serine resin successively with (1) 4.45 g., 12 mmol, of $N^\alpha$ -t-butoxycarbonyl-O-benzyl-L-tyrosine, and 2.5 g., 12.1 mmol of dicyclohexylcarbodiimide, (2) 2.5 g., 11.6 mmol, of $N^\alpha$ -t-butoxycarbonyl-D-proline and 2.5 g. of dicyclohexylcarbodiimide and (3) 2.5 g., 11.6 mmol of $N^\alpha$ -t-butoxycarbonyl-L-proline and 2.5 g., 12.1 mmol if dicyclohexylcarbodiimide as described in Example 1. The purified product is a glass $[\alpha]_D^{23} + 48°$ (c 1.05, methanol).

EXAMPLE 7

$N^\alpha$ -t-Butoxycarbonyl-L-prolyl-D-prolyl-O-benzyl-L-tyrosyl-O-benzyl-L-serinamide $N^\alpha$ -t-Butoxycarbonyl-L-prolyl-D-prolyl-O-benzyl-L-tyrosyl-O-benzyl-L-serine methyl ester, 0.5 g., is reacted with ammonia utilizing the same method and proportions given in Example 2, yielding 0.23 g. of product $[\alpha]_D^{23} + 49.5°$ (c. 1.01 methanol).

EXAMPLE 8

$N^\alpha$ -t-Butoxycarbonyl-L-prolyl-D-prolyl-O-benzyl-L-tyrosyl-O-benzyl-L-serine N-ethylamide $N^\alpha$ -t-Butoxycarbonyl-L-prolyl-D-prolyl-O-benzyl-L-tyrosyl-O-benzyl-L-serine methyl ester, 0.5 g., is reacted with ethylamine using the same method and proportions given in Example 3, yielding 0.3 g. $[\alpha]_D^{23} + 51.5°$ (c. 1.05, methanol).

EXAMPLE 9

$N^\alpha$ -t-Butoxycarbonyl-L-prolyl-D-prolyl-O-benzyl-L-tyrosyl-O-benzyl-L-serine hydrazide $N^\alpha$ -t-Butoxycarbonyl-L-prolyl-D-prolyl-O-benzyl-L-tyrosyl-O-benzyl-L-serine methyl ester, 0.3 g., is dissolved in 20 ml. of ethyl alcohol and treated with 1 g. of hydrazine hydrate. The reaction is let stand at room temperature for 20 hours, then warmed to 70° C, for 1 hour. The solvent is removed under reduced pressure and the product purified by precipitation several times from an ethanol solution, 0.19 g.; $[\alpha]_D^{25} + 41°$ (c. 1, methanol).

EXAMPLE 10

$N^\alpha$ -t-Butoxycarbonyl-D-prolyl-L-prolyl-O-benzyl-L-tyrosyl-O-benzyl-L-serine methyl ester The ester is obtained by reacting 10 g. of $N^\alpha$ -t-butoxycarbonyl-O-benzyl-L-serine resin successively with 4.45 g., 12 mmol, of $N^\alpha$ -t-butoxycarbonyl-L-tyrosine, 2.5 g., 11.6 mmol, $N^\alpha$ -t-butoxycarbonyl-L-proline and 2.5 g., 11.6 mmol, $N^\alpha$ -t-butoxycarbonyl-D-proline as described in Example 1. The purified product is a glass $[\alpha]_D^{23} -26.0°$ (c 1.05, methanol).

EXAMPLE 11

$N^\alpha$ -t-Butoxycarbonyl-D-prolyl-L-prolyl-O-benzyl-L-tyrosyl-O-benzyl-L-serinamide $N^\alpha$ -t-Butoxycarbonyl-D-prolyl-L-prolyl-O-benzyl-L-tyrosyl-O-benzyl-L-serine methyl ester is reacted with ammonia utilizing the same method and proportions given in Example 2, yielding 0.3 g. $[\alpha]_D^{23} -19.4°$ (c. 1.02, methanol).

EXAMPLE 12

$N^\alpha$ -t-Butoxycarbonyl-D-prolyl-L-prolyl-O-benzyl-L-tyrosyl-O-benzyl-L-serine N-ethylamide $N^\alpha$ -t-Butoxycarbonyl-D-prolyl-L-prolyl-O-benzyl-L-tyrosyl-O-benzyl-L-serine methyl ester is reacted with ethylamine utilizing the same method and proportions given in Example 3, yielding 0.3 g., $[\alpha]_D^{23} -18.5°$ (c. 1.05, methanol).

EXAMPLE 13

$N^\alpha$ -t-Butoxycarbonyl-D-prolyl-L-prolyl-O-benzyl-L-tyrosyl-O-benzyl-L-serine hydrazide $N^\alpha$ -t-Butoxycarbonyl-D-prolyl-L-prolyl-O-benzyl-L-tyrosyl-O-benzyl-L-serine methyl ester is reacted with hydrazine hydrate utilizing the method and proportions given in Example 9, yielding 0.21 g., $[\alpha]_D^{23} -18.8°$ (c. 1.05, methanol).

EXAMPLE 14

$N^\alpha$ -t-Butoxycarbonyl-D-prolyl-D-prolyl-O-benzyl-L-tyrosyl-O-benzyl-L-serine methyl ester The ester is obtained by reacting 10 g. of $N^\alpha$ -t-butoxycarbonyl-O-benzyl-L-serine resin successively with 4.45 g., 12 mmol, of $N^\alpha$ -t-butoxycarbonyl-O-benzyl-L-tyrosine, 2.5 g., 11.6 mmol, of $N^\alpha$ -t-butoxycarbonyl-D-proline and 2.5 g. of $N^\alpha$ -t-butoxycarbonyl-D-proline as described in Example 1. The crude ester is purified by chromatography over silica in ethyl acetate solution and is a glass $[\alpha]_D^{23} + 54.5°$ (c. 1.05, methanol); yield 4.2 g.

EXAMPLE 15

$N^\alpha$ -t-Butoxycarbonyl-D-prolyl-D-prolyl-O-benzyl-L-tyrosyl-O-benzyl-L-serine N-ethylamide $N^\alpha$ -t-Butoxycarbonyl-D-prolyl-D-prolyl-O-benzyl-L-tyrosyl-O-benzyl-L-serine methyl ester is reacted with ethylamine using the same method and proportions given in Example 3, yielding 0.25 g., $[\alpha]_D^{23} + 51°$ (c. 1.03, methanol).

EXAMPLE 16

N$^\alpha$-t-Butoxycarbonyl-D-prolyl-D-prolyl-O-benzyl-L-tyrosyl-O-benzyl-L-serine hydrazide N$^\alpha$-t-Butoxycarbonyl-D-prolyl-D-prolyl-O-benzyl-L-tyrosyl-O-benzyl-L-serine methyl ester is reacted with hydrazine hydrate, utilizing the same method and proportions given in Example 9, yielding a granular solid $[\alpha]_D^{23}$ + 55.5° (c. 1.01, methanol).

EXAMPLE 17

N$^\alpha$-Cyclohexylcrbonyl-L-prolyl-L-prolyl-O-benzyl-L-tyrosyl-O-benzyl-L-serine methyl ester O-Benzyl-L-serine resin, 20 g., is coupled successively according to general procedure of Example 1 with (1) 26.7 g., 72 mmol, of N$^\alpha$-t-butoxycarbonyl-O-benzyl-L-tyrosine and 7.5 g. of dicyclohexylcarbodiimide, (2) 24.5 g., 72 mmol, of N$^\alpha$-t-butoxycarbonyl-L-proline and 7.5 g. of dicyclohexylcarbodiimide, (3) 24.5 g., of N$^\alpha$-t-butoxycarbonyl-L-proline and 7.5 g. of dicyclohexylcarbodiimide and (4) 9.2 g., 72 mmol, of cyclohexane carboxylic acid and 7.5 g. of dicyclohexylcarbodiimide. The resulting N$^\alpha$-cyclohexylcarbonyl-L-prolyl-L-prolyl-O-benzyl-L-tyrosyl-O-benzyl-L-serine resin is stirred with 250 ml. of methanol and 25 ml. of triethylamine at room temperature for 24 hours. After filtration and evaporation, the crude product is chromatographed on silica gel with 5% methanol in ethyl acetate, 5.4 g.; $[\alpha]_D^{25}$ −60° (c. 1.0, methanol).

EXAMPLE 18

N$^\alpha$-Cyclohexylcarbonyl-L-prolyl-L-prolyl-O-benzyl-L-tyrosyl-O-benzyl-L-serine N-ethylamide The methyl ester of Example 17, 0.5 g., is stirred in 25 ml. of 50% ethylamine in methanol for 24 hours at room temperature. After evaporation, the product is chromatographed on silica gel with 10% methanol in ethyl acetate yielding 240 mg. of product; $[\alpha]_D^{25}$ −61.5° (c. 1.0, methanol).

EXAMPLE 19

N$^\alpha$-Cyclohexylcarbonyl-L-prolyl-L-prolyl-O-benzyl-L-tyrosyl-O-benzyl-L-seryl hydrazide The methyl ester of Example 17, 0.5 g. is stirred in a solution of 1 ml. of hydrazine hydrate and 10 ml. of ethanol. The solution is warmed to 90° C. for 1 hour and let stand at room temperature overnight. The precipitate is collected and re-precipitated from methanol with ether yielding 130 mg. of product; $[\alpha]_D^{25}$ −66° (c. 1.0, methanol).

EXAMPLE 20

N$^\alpha$-Cyclohexylcarbonyl-L-prolyl-L-prolyl-O-benzyl-L-tyrosyl-O-benzyl-L-serinamide The methyl ester of Example 17, 0.5 g., is stirred in 20 ml. of methanol saturated with ammonia for three days at room temperature. After evaporation, the product is chromatographed on silica gel with 15% methanol in ethyl acetate; $[\alpha]_D^{25}$ −67° (c. 1.0, methanol).

I claim:

1. A tetrapeptide represented by the formula

A-Pro-Pro-Tyr(benzyl)-Ser(benzyl)-R$_1$ wherein A is t-butoxycarbonyl, cyclohexylcarbonyl, benzyloxycarbonyl or p-nitro-benzyloxycarbonyl; Pro is L-Pro or D-Pro, Tyr(benzyl) is L-Tyr(benzyl) or D-Tyr(benzyl), Ser(benzyl) is L-Ser-(benzyl) or D-Ser(benzyl), and R$_1$ is lower alkoxy, hydrazino, amino, lower alkylamino or di(lower alkyl)amino.

2. The compound of claim 1 having the name N$^\alpha$-t-butoxycarbonyl-L-prolyl-L-prolyl-O-benzyl-L-tyrosyl-O-benzyl-D-serine N-ethylamide.

3. The compound of claim 1 having the name N$^\alpha$-cyclohexylcarbonyl-L-prolyl-L-prolyl-O-benzyl-L-tyrosyl-O-benzyl-L-serine methyl ester.

4. The compound of claim 1 having the name N$^\alpha$-t-butoxycarbonyl-L-prolyl-L-prolyl-O-benzyl-L-tyrosyl-O-benzyl-D-serine methyl ester.

5. The compound of claim 1 having the name N$^\alpha$-t-butoxycarbonyl-D-prolyl-D-prolyl-O-benzyl-L-tyrosyl-O-benzyl-D-serine methyl ester.

6. The compound of claim 1 having the name N$^\alpha$-t-butoxycarbonyl-L-prolyl-D-prolyl-O-benzyl-L-tyrosyl-O-benzyl-L-serine N-ethylamide.

7. The compound of claim 1 having the name N$^\alpha$-t-butoxycarbonyl-D-prolyl-D-prolyl-O-benzyl-L-tyrosyl-O-benzyl-L-serine methyl ester.

8. The compound of claim 1 having the name N$^\alpha$-t-butoxycarbonyl-D-prolyl-D-prolyl-O-benzyl-L-tyrosyl-O-benzyl-L-serine hydrazide.

* * * * *